(12) United States Patent
Swank

(10) Patent No.: US 11,701,252 B1
(45) Date of Patent: Jul. 18, 2023

(54) THERMAL PAD JOINING SYSTEM

(71) Applicant: Scott Swank, Tampa, FL (US)

(72) Inventor: Scott Swank, Tampa, FL (US)

(*) Notice: Subject to any disclaimer, the term of this patent is extended or adjusted under 35 U.S.C. 154(b) by 0 days.

(21) Appl. No.: 17/986,642

(22) Filed: Nov. 14, 2022

(51) Int. Cl.
*A61F 7/08* (2006.01)
*A61F 7/00* (2006.01)

(52) U.S. Cl.
CPC ........ *A61F 7/08* (2013.01); *A61F 2007/0054* (2013.01); *A61F 2007/0056* (2013.01)

(58) Field of Classification Search
CPC ............... A61F 7/08; A61F 2007/0056; A61F 2007/0054
See application file for complete search history.

(56) References Cited

U.S. PATENT DOCUMENTS

| | | |
|---|---|---|
| 2,606,005 A | 8/1952 | Puox |
| 8,172,888 B1 | 5/2012 | Beavers et al. |
| 11,154,419 B2 | 10/2021 | Miller et al. |
| 2006/0178717 A1 | 8/2006 | Harris et al. |
| 2008/0119916 A1 | 5/2008 | Choucair et al. |
| 2015/0216721 A1* | 8/2015 | Thacker ............ A61D 9/00 607/114 |
| 2016/0213508 A1 | 7/2016 | Sherman |
| 2018/0243127 A1* | 8/2018 | Chavarry ............ A61F 7/02 |
| 2019/0133816 A1 | 5/2019 | Planchon et al. |

FOREIGN PATENT DOCUMENTS

| | | |
|---|---|---|
| DE | 202010000829 U1 | 4/2011 |
| KR | 200455235 Y1 | 8/2011 |
| KR | 20120007666 | 1/2012 |
| KR | 20190108341 | 9/2019 |
| KR | 102114465 | 5/2020 |
| KR | 20220004289 | 1/2022 |
| WO | 1993024797 | 12/1993 |
| WO | 2010060931 | 6/2010 |
| WO | 2020239173 | 12/2020 |

* cited by examiner

*Primary Examiner* — Tigist S Demie
(74) *Attorney, Agent, or Firm* — The Concept Law Group, PA; Scott D. Smiley; Scott M. Garrett

(57) ABSTRACT

A thermal pad system is disclosed in which two or more thermal pads can be connected together to cover a larger region of the body than a single pad, and the joining is done in such a way that there is substantially no gap between the volumes of thermal material in each pad on the side of the pads that is applied to the user's body. Each thermal pad is substantially flat, and includes a fringe portion around a volume of thermal material, wherein the two sides are joined together to create a liquid barrier. A joining clip is used to connect two thermal pads together by lifting the fringe portions along corresponding edges of the two pads away from the side of the pads to be applied to the body, and the joining clip is configured to not just hold the fringe portion sections together, but also to urge the two volume portions together under the joined fringe portion sections.

17 Claims, 13 Drawing Sheets

THERMAL PAD JOINING SYSTEM

FIELD OF THE INVENTION

The present invention relates generally to thermal pad used to reduce inflammation and sooth body portions, and, more particularly, relates to a system of thermal pads that can be interconnected in a way that leaves no gap between the thermal pads, and which allows the thermal pads to conform to the shape of the body where they are applied.

BACKGROUND OF THE INVENTION

It is well known the applying heat or cold to various types of injuries and chronically aggravated musculo-skeletal portions of the body can alleviate pain and inflammation. The recency of the injury will often dictate whether heat or cold is better. Accordingly, people have used, for example, warm moist towels, heating pads, ice blocks, and other articles and devices to apply heat or cold to injured or inflamed body regions. These all have various drawbacks, such as ice melting and dripping water as well as being rigid in the case of ice blocks, the need for an electric outlet in the case of heating pads, and so on. More recently thermal pads have been developed that alleviate many of the problems with prior art thermal articles. Thermal pads are generally flat articles having a compliant polymeric skin that contains a thermal material. Thermal material can be warmed or chilled, and will still flow and therefore allow the pad to take on the shape of the body region to which it is applied.

Accordingly, thermal pads have been found to be very useful for treating injured and inflamed body regions. However, thermal pads are sold in various discrete sizes that may not be large enough, or may be too large for a given application. People have used multiple thermal pads to cover larger regions, but often these have to be held together with bandages or other such means, and typically there are gaps between the pads that can reduce the effectiveness of the application of heat or cold to the injured or inflamed body region.

Therefore, a need exists to overcome the problems with the prior art as discussed above.

SUMMARY OF THE INVENTION

In accordance with some embodiments of the inventive disclosure, there is provided a modular thermal pad system that includes a plurality of thermal pads. Each one of the thermal pads has a first side and a second side. The sides define a sealed volume between them, and they are joined together around a perimeter of the sealed volume. There is thermal material disposed in the sealed volume for each of the thermal pads. Thermal material is a non-gaseous, non-solid material, which can include fluids or gels. Each of the pads also includes a fringe which extends from the perimeter of the sealed volume to an edge. The fringe is made of the material of each of the two sides being laid, one on top of the other, and joined together, such as by heat treatment or glue. Thus, where the sealed volume is a portion of the thermal pad in which the two sides of the thermal pad are not joined directly to each other in order to allow the thermal material between them, the fringe is a portion where the two sides are directly bonded or joined together. The two sides are generally sheets or material such as a polymeric material that bends easily, nearly like a fabric. The fringe of each of the thermal pads has at least one linear section disposed along a linear edge. That is, the linear section includes a straight edge in a direction around the perimeter. The linear section of the fringe has at least one opening through it which is located at a first distance from the perimeter. The system further includes a (one or more) joining clip having a first portion and a second portion. Each of the first and second portions of the joining clip have a planar surface. The first portion of the joining clip has one or more posts extending perpendicularly from the planar surface. The post has a diameter that is about equal to a diameter of the hole or opening through the fringes of the thermal pads, and is sized to pass through the opening in the fringes. The second portion of the joining clip has an opening there through that is sized to receive the post of the first portion of the joining clip in a snap-fit manner to retain the post. When the first thermal pad and a second thermal pad are positioned adjacent to each other with a fringe of the first thermal pad placed against the fringe of the second thermal pad, the joining clip holds the fringe of the first thermal pad and the fringe of the second thermal pad together on one side of the first and second thermal pads such that on a second side of the first and second thermal pads, that is opposite the first side, the sealed volume of the first thermal pad abuts the sealed volume of the second thermal pad such that there is little to no gap between the pads on the second side. The geometry of the joining clip is inherently such that it gathers so much of the fringes together on one side that it pulls the pads together such that their respective thermal material volumes are directly adjacent each other on the side opposite from the joining clip.

In accordance with a further feature, the first and second thermal pads have a hexagonal shape.

In accordance with a further feature, the thermal material is a liquid.

In accordance with a further feature, there is further included a first strap clip disposed at an edge of the first thermal pad and a second strap clip disposed at an edge of the second thermal pad.

In accordance with some embodiments of the inventive disclosure, there is provided a modular thermal pad system that includes at least two thermal pads. There is at least a first thermal pad and a second thermal pad which each have a substantially flat body including a first side member and a second side member. Each of the first and second side members are comprised of a respective sheet of material. The first and second side members define a sealed volume between them which is bounded by a border around the sealed volume where the first side member and the second side member are joined (bonded) together. The sealed volume of each of the at least two thermal pads is filled with a thermal material. There is also a fringe extending from the border in an outward direction relative to the sealed volume and the fringe includes a plurality of linear sections around the fringe. Each linear section includes at least one opening through the linear section that is spaced a first distance from the border of the sealed volume. There is also a joining clip that has a first portion and a second portion. The first portion has a flat body and at least one post extending perpendicularly from the first portion. The second portion has a flat body and at least one hole through the second portion. The at least one post is spaced the first distance (i.e. the same distance as the distance from the hole/opening through the fringe to the border of the sealed volume) from an edge of the first portion. The at least one hole is also spaced the first distance from an edge of the second portion. The joining clip is configured to hold a fringe portion of the first thermal pad together with a corresponding fringe portion of the second thermal pad on a first side of the first and second thermal pads such that the sealed volume of the first thermal pad abuts the sealed volume of the second thermal pad on a second side of the first and second thermal pads.

In accordance with a further feature, the thermal material in each of the at least two thermal pads is a fluid.

In accordance with a further feature, the border and fringe of each of the at least two thermal pads are shaped in a regular polygon shape.

In accordance with a further feature, the regular polygon shape is a hexagon.

In accordance with a further feature, each of the plurality of linear sections of the fringe of each of the at least two thermal pads includes at least two openings.

In accordance with a further feature, the first and the second portion of the joining clip are coupled together by at least one hinge portion.

In accordance with a further feature, there is further included a first strap clip disposed at an edge of a first thermal pad of the at least two thermal pads, and a second strap clip disposed at an opposite edge of a second thermal pad of the at least two thermal pads, wherein each of the first and second strap clips include a post that passes through an opening at the fringe on each of the edge and the opposite edge.

In accordance with some embodiments of the inventive disclosure, there is provided a thermal pad system there is included a first thermal pad and a second thermal pad. Each of the first and second thermal pads included a first side and a second side. There is also a volume formed between the first side and the second that contains a thermal material. The volume is defined (bordered) by a border that is sealed around the volume at a perimeter of the volume. Each thermal pad also includes a fringe that extends outward from the perimeter of the volume to an edge. The edge represents the ends of the two side members forming the thermal pad. There is also a joining clip that gathers a portion of the fringe of the first thermal pad and a portion of the fringe of the second thermal pad together on a same side of the first and second thermal pads and which, as a result, forces the volume of the first thermal pad to abut the volume of the second thermal pad on the opposite side of the first and second thermal pads from the joining clip.

In accordance with a further feature, the portion of the fringe of the first thermal pad and the portion of the fringe of the second thermal pad gathered by the joining clip each have a hole that is spaced a first distance from the perimeter of the volume of the first and second thermal pads, respectively. The joining clip has a first portion and a second portion, the first portion having a flat body and at least one post extending perpendicularly from the first portion, the second portion having a flat body and at least one hole through the second portion, and wherein the at least one post is spaced the first distance from an edge of the first portion, and the at least one hole is spaced the first distance from an edge of the second portion.

In accordance with a further feature, the first and the second portion of the joining clip are coupled together by at least one hinge portion.

In accordance with a further feature, the first and second thermal pads have a hexagonal shape.

In accordance with a further feature, the thermal material is a liquid.

In accordance with a further feature, there is further included a first strap clip disposed at an edge of the first thermal pad and a second strap clip disposed at an edge of the second thermal pad.

Although the invention is illustrated and described herein as embodied in a thermal pad system, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

"In the description of the embodiments of the present invention, unless otherwise specified, azimuth or positional relationships indicated by terms such as "up", "down", "left", "right", "inside", "outside", "front", "back", "head", "tail" and so on, are azimuth or positional relationships based on the drawings, which are only to facilitate description of the embodiments of the present invention and simplify the description, but not to indicate or imply that the devices or components must have a specific azimuth, or be constructed or operated in the specific azimuth, which thus cannot be understood as a limitation to the embodiments of the present invention. Furthermore, terms such as "first", "second", "third" and so on are only used for descriptive purposes, and cannot be construed as indicating or implying relative importance.

In the description of the embodiments of the present invention, it should be noted that, unless otherwise clearly defined and limited, terms such as "installed", "coupled", "connected" should be broadly interpreted, for example, it may be fixedly connected, or may be detachably connected, or integrally connected; it may be mechanically connected, or may be electrically connected; it may be directly connected, or may be indirectly connected via an intermediate medium. As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" and "elongated" should be understood to mean in a direction corresponding to an elongated direction of the article being described. Those skilled in the art can understand the specific meanings of the above-mentioned terms in the embodiments of the present invention according to the specific circumstances.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
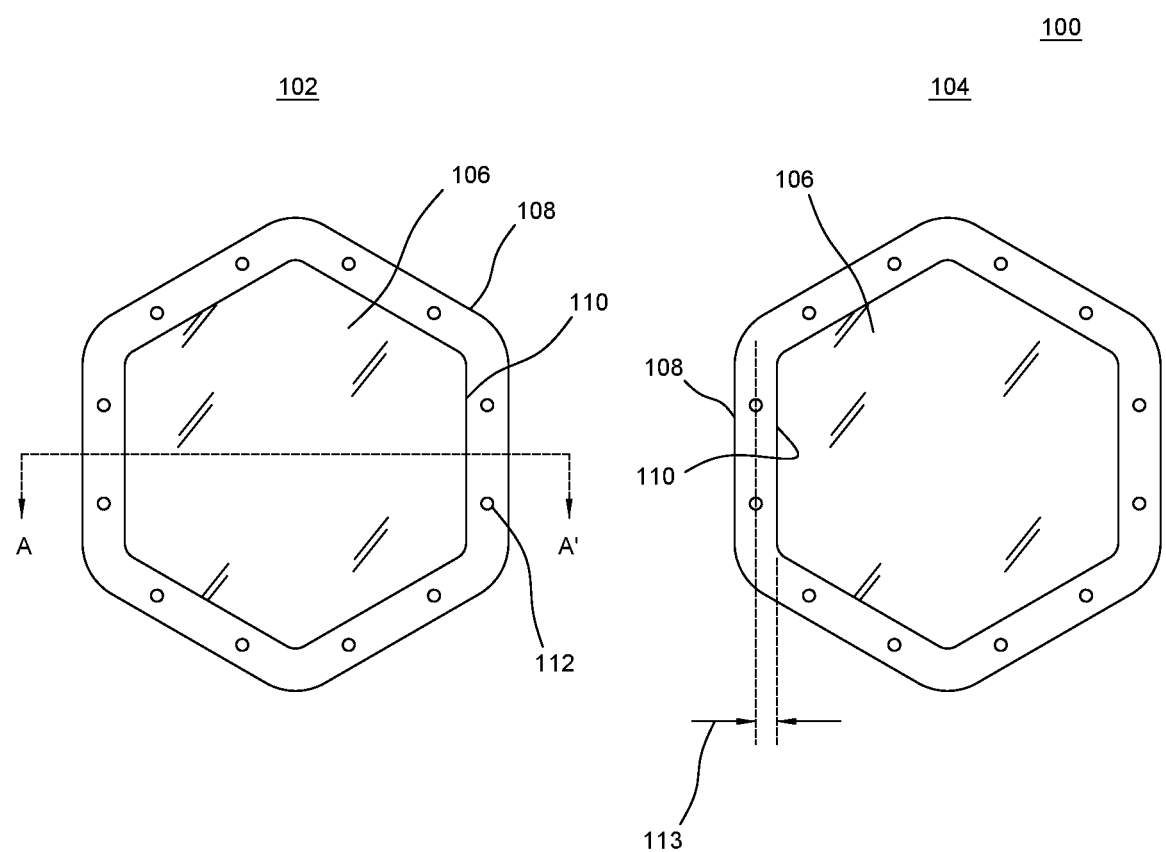
FIG. 1 a plan view of a pair of thermal pads used in the inventive thermal pad system, in accordance with some embodiments.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient thermal pad system that allows a user to configure several smaller thermal pads together in a desired shape for a application to a specific region of the body. Individual thermal pads can be joined or fastened together in a way that allows both construction of a desired shape, and which leaves no gaps between the pads. This provides an advantage over the use of individual pads having a set shape, as well as systems in which thermal elements are joined together but which leave substantial gaps between the thermal elements.

FIG. 1 a plan view of a pair of thermal pads 102, 104 used in the inventive thermal pad system 100, in accordance with some embodiments. In general, the thermal pads 102, 104 are examples of one configuration thermal pads that can be used in the system 100 of a plurality of such thermal pads. At least two thermal pads are used, but others can be added in order achieve the desired shape for application to a specific region of the body. Each of the thermal pads 102, 104 includes a substantially flat body portion 106 that contains a thermal material, such as a gel or liquid. The thermal material can be a fluidic material that has a relatively high specific heat and that doesn't freeze or boil at temperature ranges useful for thermal treatment by direct application to the human body. The thermal material can be selected for particular applications in some embodiments. For example, for applying heat, the pads can be filled with water or a mostly water mix as water has a relative high specific heat. Other types of thermal materials can be used equivalently, or to cover a wider temperature range. The thermal material is captured between two sides forming the opposing major surfaces. The two sides are each made of a sheet of a compliant material that are fluid impermeable barriers to contain the thermal material, as well as exclude moisture and other chemical contaminants from entering the thermal pad. The two side members define a space between them that is bounded by a border 110. The thermal material is provided between the two side members and within the border. The border 110 forms a perimeter around the space in which the thermal material is disposed and is defined by at least one straight section of the perimeter. The two sides are bonded together at the border 110, and form a fringe 108 that extends outward from the border 110 where the two sides are bonded together. The fringe 108 is therefore flat and contains no thermal material. However at each side of the pads 102, 104 there are a pair of holes or openings 112 through the fringe 108. The holes 112 are all located a specific distance 113 from the border 110 along a straight section of the border, and this spacing is consistent around the entirely of the fringe 108 where there are straight sections of the border 110, and on all thermal pads in the system. As shown here, the pad 102, 104 have a hexagonal shape, with the border 110 having six straight sides of substantially equal length. As a result, the fringe 108 also has six corresponding sections, where each section has a pair of holes 112. The fringe 108 and holes 112 are used to gather the pads 102, 104 together, as will be described.

Figure 2:
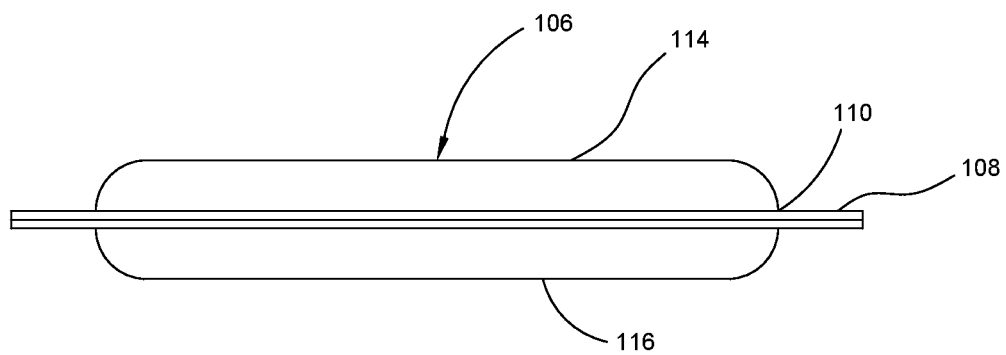
FIG. 2 shows a side view of a thermal pad for use in a thermal pad system, in accordance with some embodiments.
Figure 3:
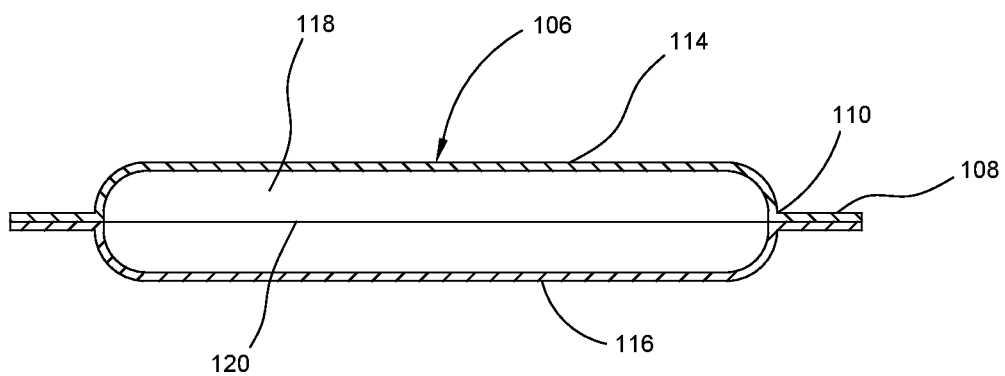
FIG. 3 shows a side section cut-away view of a thermal pad for use in a thermal pad system, in accordance with some embodiments.

FIG. 2 shows a side view of a thermal pad 102 for use in a thermal pad system, in accordance with some embodiments. The thermal pad 102 includes a first side member 114 and a second side member 116 that form opposite major surfaces of the generally flat body portion 106. The side members 114, 116 are formed by sheet-like members that are joined together around a border 110 that forms a perimeter of an internal volume between the side members 114, 116 in which a thermal material is disposed. The fringe 108 extends from the border 110 laterally, and is formed by the materials of both side members 114, 116 being bonded together. FIG. 3 shows a side section cut-away view of a thermal pad 102 for use in a thermal pad system, in accordance with some embodiments. The view here is taken along section line A-A' in FIG. 1. As can be seen, thermal material 118 is disposed between side members 114, 116 which meet at, and are joined along seam 120. Accordingly, the thermal pads 102, 106 act as bladders that contain the thermal material. The thermal pads 102, 104 each have a generally flat body that provides two major opposing surfaces and defines a plane when the thermal pads are laid on a flat level surface. The fact that there is a thermal material sealed in the space between the two side members 114, 116 means that the two sides of the body 106 are not perfectly flat as there are contours around the border 110. Further, because the material of the side members 114, 116 are supple, and the thermal material can be a gel or liquid, the thermal pad 102 is supple and can conform to various shapes of the body. Thus, when the body 106 is described as substantially flat, it is meant that when the thermal pad 102 is placed on a flat level surface, the body 106 will likewise have a generally flat configuration. When used, however, the thermal pad 102 can be conformed into virtually any shape that does not stress the materials of the side members 114, 116 to the point of rupture.

Figure 4:
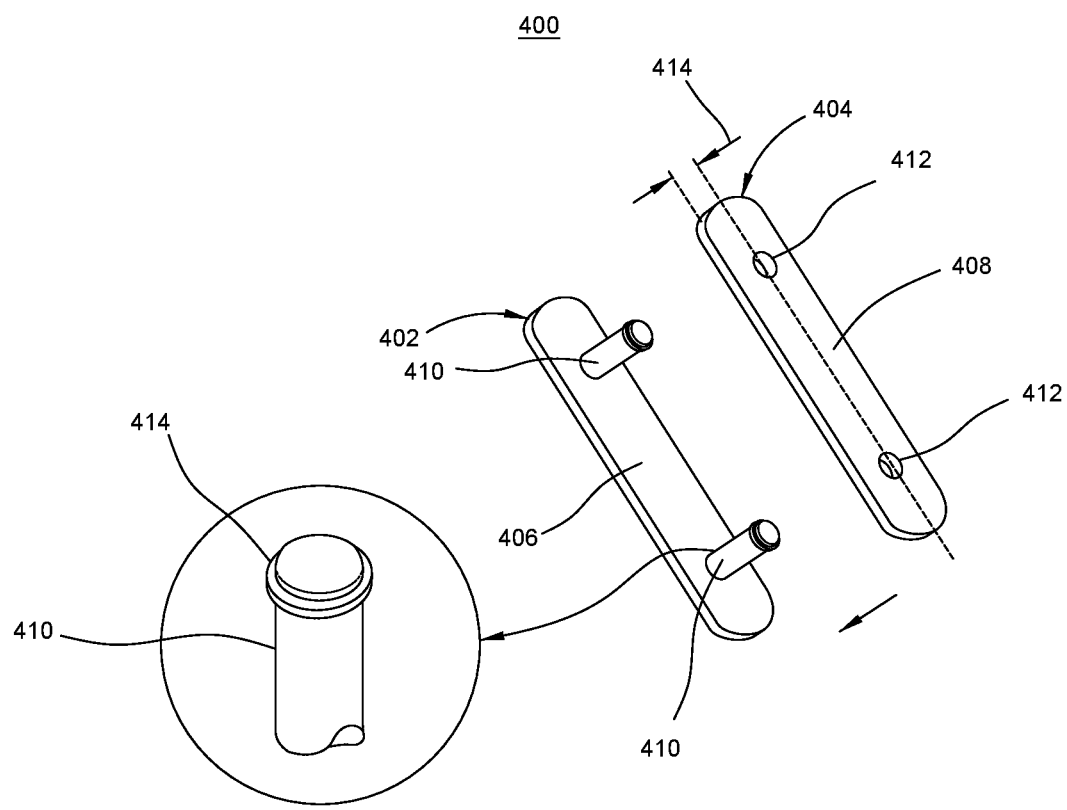
FIG. 4 shows a perspective view of a clip for joining thermal pads together in a thermal pad system, in accordance with some embodiments.

FIG. 4 shows a perspective view of a joining clip 400 for joining thermal pads together in a thermal pad system, in accordance with some embodiments. The joining clip 400 includes a first portion 402 and a second portion 404. The first portion 402 has a generally elongated flat body 406 from which a pair of posts 410 protrude in a generally perpendicular direction from the body 406. The posts are spaced apart from each other by a distance equal to the distance between holes 112 in the fringe 108 of the thermal pads 102, 104. The second portion 404 of the joining clip also has an elongated and generally flat body 408 that has two holes 412 through the body that are sized to allow the posts 410 to pass through the holes 412. The holes 412 and the posts 410 are centered along the respective portions 404, 402 relative to the elongated edge at a distance 414 that is substantially equal to the distance 113 between the holes 112 in the fringe 108 of the thermal pads 102, 104 and the border 110. The posts 410 can be formed to have a slightly enlarged diameter at their distal end 414 that creates an interference with the body 408 around the holes 412 so as to retain the second portion 404 on the posts 410 in a semi-permanent manner where a user could pull the second portion 402 off of the posts 410 without damaging either the posts 410 or the second portion 404 of the joining clip. As a result, the two portions of the joining clip 400 have a snap-fit retention. As the enlarged distal end of the posts 410 are pushed through the hole there is resistance initially until the force overcomes the resistance, resulting in an audible "snap" as the enlarged distal end of the post 410 passes through the hole and comes out on the other side of the second portion 404.

Figures 5A, 5B, 5C:
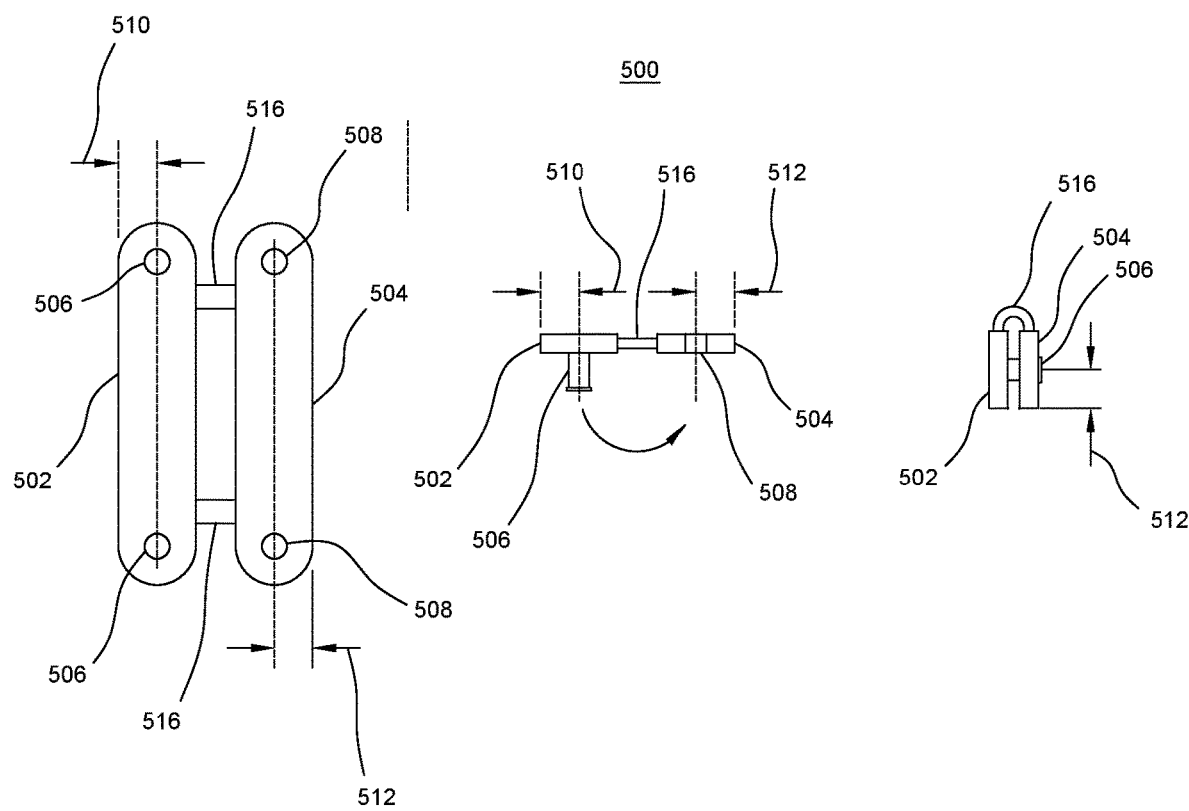
FIG. 5A shows a plan view of a clip for joining thermal pads together in a thermal pad system, in accordance with some embodiments.
FIG. 5B shows an end view of a clip for joining thermal pads together in a thermal pad system, with the clip open, in accordance with some embodiments.
FIG. 5C shows an end view of a clip for joining thermal pads together in a thermal pad system, with the clip closed, in accordance with some embodiments.

FIG. 5A shows a plan view of a joining clip 500 for joining thermal pads together in a thermal pad system, in accordance with some embodiments. Joining clip 500 differs from joining clip 400 in that hinge portions 516 join two portions 502, 504 together. First portion 502 includes a generally elongated and planar body that has posts 506 that extend from the body perpendicular to the plane of the body. The second portion 504 likewise comprises a generally planar and elongated body that has holes 508 formed therethrough, and that are sized to receive the distal end of the posts 506. FIG. 5B shows an end view of the joining clip 500, and FIG. 5C shows an end view of a clip 500 with the joining clip 500 closed, in accordance with some embodiments. The posts 506 are centered to be a distance 510 from the outer edge of portion 502, and holes 508 are likewise a distance 512 from the outer edge of the portion 504, where the distances 510, 512 are equal to each other, and equal to distance 113. As in joining clip 400, the distal end of posts 506 can have an enlarge diameter relative to the main shaft of the post so as to create an interference with material of portion 504 around holes 508.

Figure 6A:
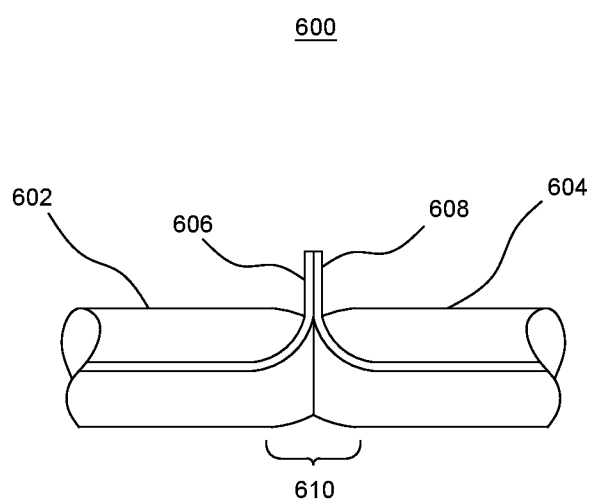
FIG. 6A shows a side view of two thermal pads arranged side to side to be joined or fastened together in a thermal pad system, in accordance with some embodiments.
Figure 6B:
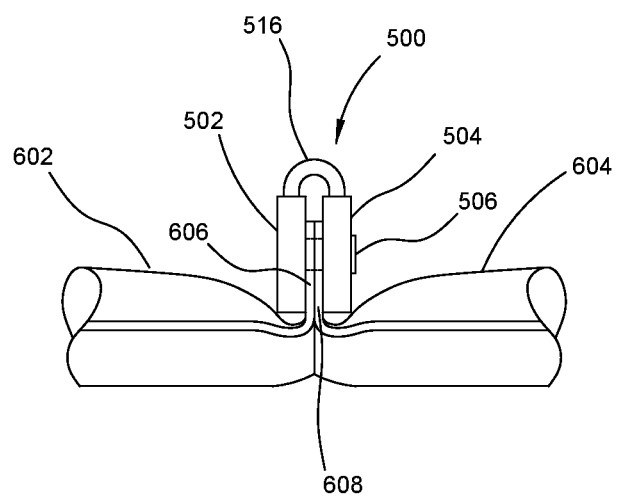
FIG. 6B shows a side view of two thermal pads that are joined or fastened together in a thermal pad system, using a clip, in accordance with some embodiments.

FIG. 6A shows a side view of two thermal pads 602, 604 arranged side to side to be joined or fastened together in a thermal pad system. Thermal pads 602, 604 can be identical to thermal pads 102, 104 or have some other shape or configuration. To join two thermal pads 602, 604 together in the system 600, the fringes 606, 608 of two pads 602, 604 are lifted at a perpendicular angle from the general plane of the body of each pad 602, 604, and placed together so that the holes of each pad are aligned. By placing the fringes 606, 608 together and perpendicular to the general planar body of each pad 602, 604, there is no gap at the bottom 610, opposite the fringes 606, 608, between the volumes of the two pads 602, 604 containing the thermal material. A joining clip can be used to hold the pads in this position, as is shown in FIG. 6B, which shows a side view of two thermal pads 602, 604 that are joined or fastened together in a thermal pad system, using a joining clip 500. The posts 506 are passed through the holes 508 of the two abutting fringe portions 606, 608, and further through the holes 508 of the second portion 504 of the clip 500. The interference retention holds the fringes 108 together, and the spacing of the posts 410 and holes 412 from the respective edges is such that is forces the fluid-containing body portions of the two pads 102, 104 to abut each other, leaving no gap between them. As a result, the effect of the heat (or cold) provided by the thermal material inside the thermal pads 602, 604 is applied more evenly to the body region than if there was a gap between the thermal pads. As a result, the thermal pad system does not need to be periodically repositioned to ensure even application of heat or cold as would be necessary when there are gaps between the thermal pads.

Figure 7A:
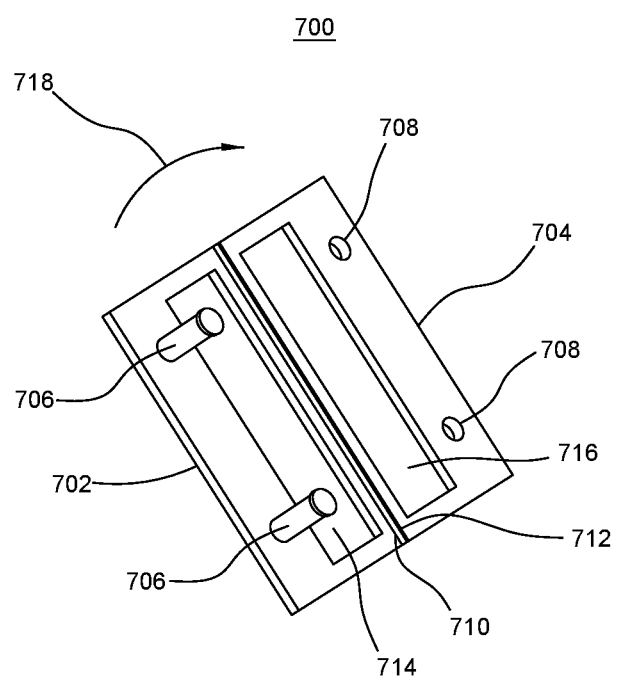
FIG. 7A shows a strap clip in an open position for attaching a strap to a thermal pad in a thermal pad system, in accordance with some embodiments.
Figure 7B:
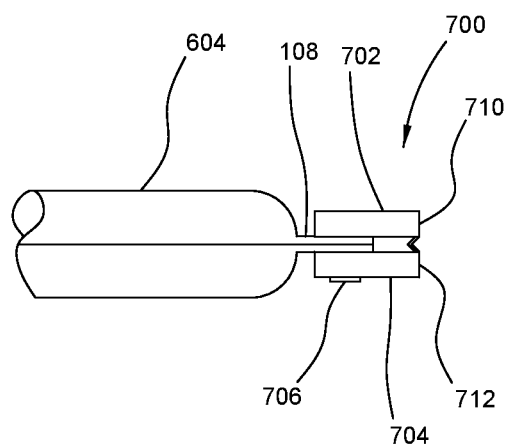
FIG. 7B shows a side view of a thermal pad having a strap clip fastened to, in a thermal pad system, in accordance with some embodiments.

FIG. 7A shows a strap clip 700 in an open position for attaching a strap to a thermal pad in a thermal pad system, in accordance with some embodiments. The strap clip 700 includes a first portion 702 and a second portion 704 that is hingeably joined to the first portion 702. Each of the portions 702, 704 have a generally planar and flat body. The first portion includes one or more posts 706 that extend from the flat body of the first portion 702 that mate with holes 708 on the second body portion 704. The first body portion 702 includes a strap opening 714 that is formed by an extension 710 that extends from the main body of the first portion 702, from one end to the opposite end, and at a distance from the main body of the first portion 702 to create and enclosed opening 714. Likewise, the second portion has a similar extension 712, that forms the hinge with extension 710, and creates a corresponding strap opening 716. When the first portion 702 is moved relative to the second portion 704, as indicated by arrow 718, the material joining the extensions 710, 712 bends, allowing the posts 706 to pass through the holes 708. In FIG. 7B, the closed strap clip 700 is shown attached to the fringe 108 of a thermal pad 604. The posts 706 pass through the holes 112 in the fringe 108, and the openings 714, 716 allow a strap to pass through the strap clip 700. The posts 706 can have an enlarge diameter at their distal end to achieve an interference with the material around holes 708 so as to retain the joining clip in a closed position until a user decides to open the joining clip 700.

Figure 8A:
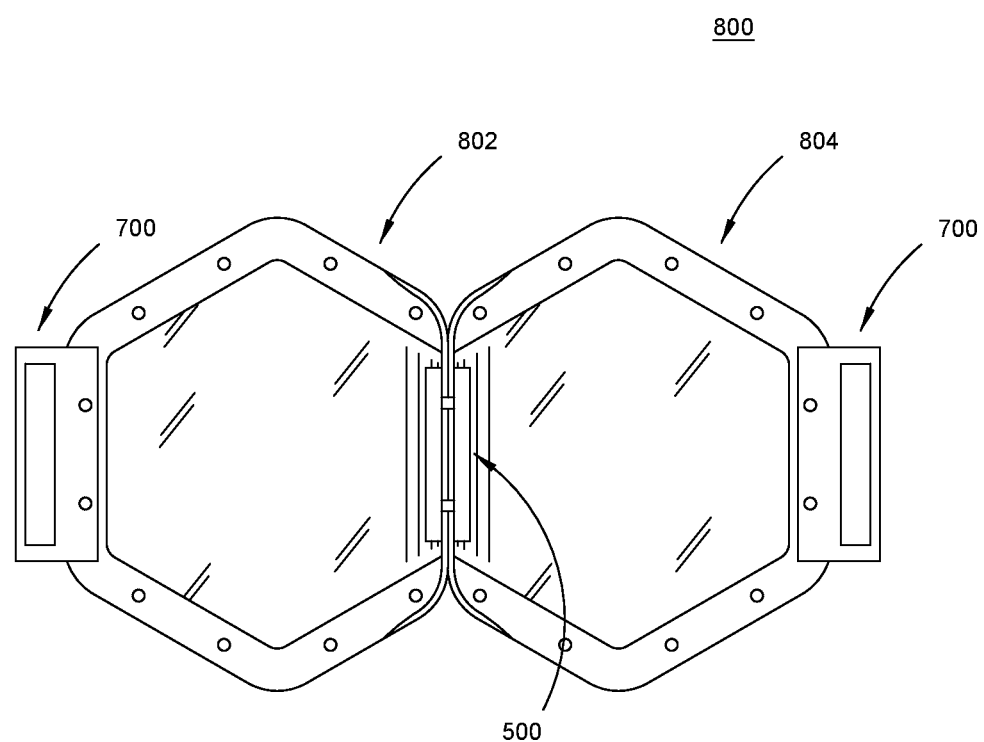
FIG. 8A shows a first side view of a pair of thermal pads that are fastened or joined together using a clip, and which have strap clips fastened to opposite sides of the thermal pads, in accordance with some embodiments.
Figure 8B:
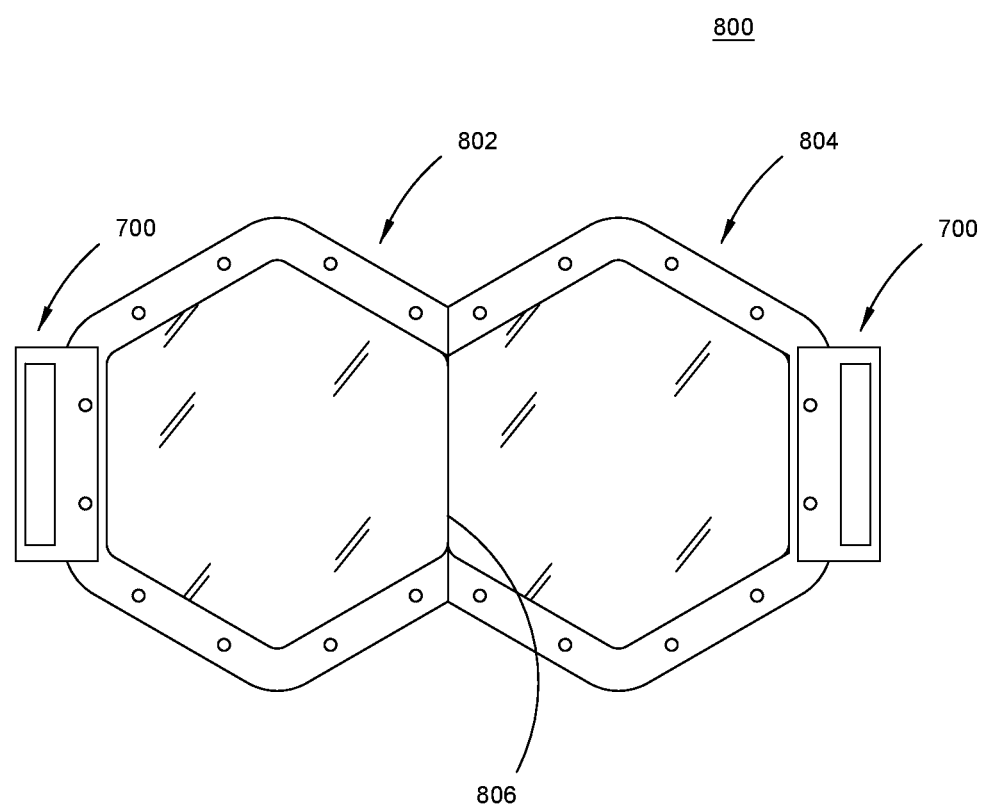
FIG. 8B shows a second side view of a pair of thermal pads that are fastened or joined together using a clip, illustrating how the pad volumes abut each other and leave no significant gap between the thermal pad, and which have strap clips fastened to opposite sides of the thermal pads, in accordance with some embodiments.
Figure 9:
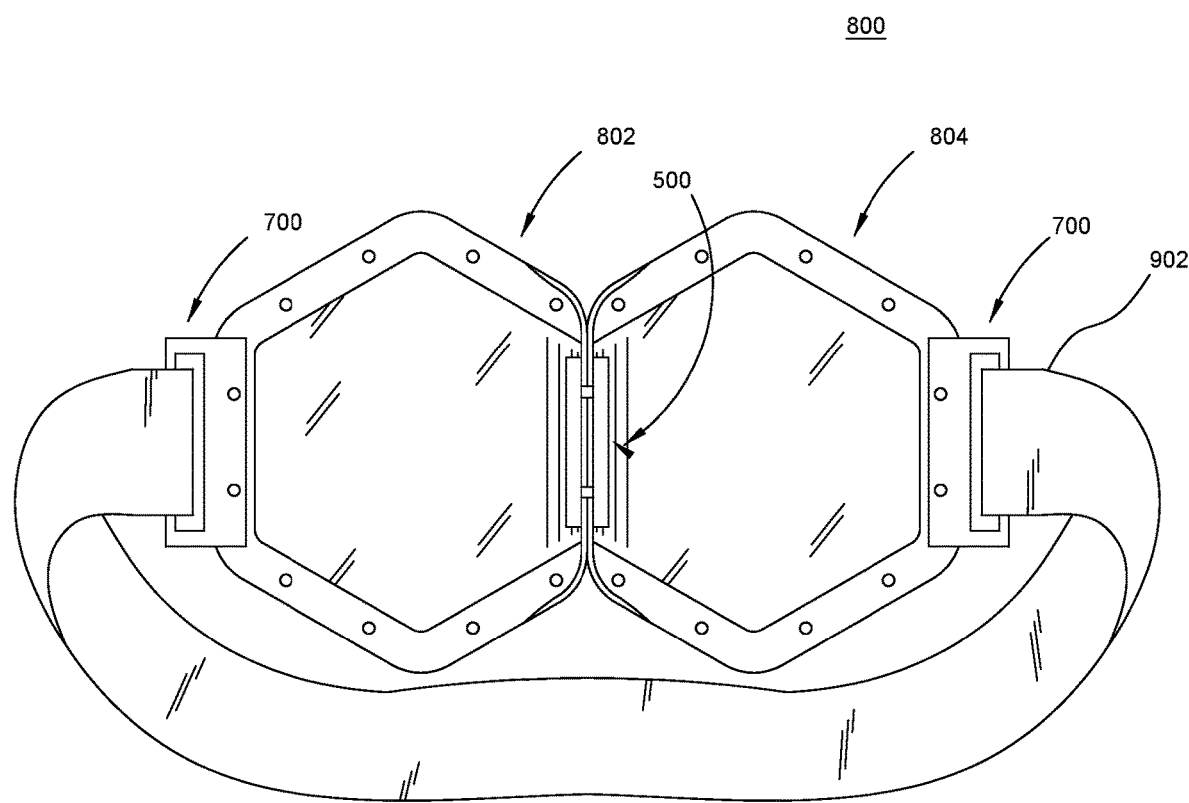
FIG. 9 shows a first side view of a pair of thermal pads that are fastened or joined together using a clip, and which have strap clips fastened to opposite sides of the thermal pads with the strap in place, in accordance with some embodiments.

FIG. 8A shows a first side view of a system 800 of thermal pads 802, 804 that are fastened or joined together using a joining clip 500, and which have strap clips 700 fastened to opposite ends of the thermal pads 802, 804, in accordance with some embodiments. The thermal pads 802, 804 can be substantially similar if not identical to thermal pads 102, 104, and include a volume of thermal material surrounded by a border, and having a fringe with openings. In FIGS. 8A and 8B the pads 802, 804 are arranged as shown in FIG. 6B, with the fringe portions bent to the same side, and the joining clip 500 used to join or fasten the two pads 802, 804 together. In addition, strap clips 700 are attached at the opposite ends of the system 800, where the joining clips are shown. It can be seen here that the joining clips 700 form a loop through which a strap can be passed strap the thermal pad system 800 in place on a person's body. In FIG. 8B, the opposite side of the system 800 is shown. Accordingly, the joining clip 500 is not in view as it is on the opposite side of the thermal pads in this view. It can be seen that, because of the dimensions of the joining clip 500 and the fringe sections of the pads 802, 804, the volume regions of the two pads 802, 804 are brought together along line 806 such that there is little to no substantial gap between the portions of the two pads 802, 804 containing the thermal material. The side of the system 800 in view here is the side that is to be applied to the affected body region for thermal therapy. The lack of any substantial gap between the pads means the user doesn't have to keep repositioning the pads to ensure the thermal therapy is sufficiently applied across the body region being treated. FIG. 9 shows a first side view of a system 800 of thermal pads 802, 804 that are fastened or joined together using a joining clip 500, and which have strap clips 700 fastened to opposite ends of the thermal pad system 800 with the strap 902 in place. The strap can be an otherwise conventional strap that allows a user to shorten or lengthen the strap 900 as is needed to reach around a body region and hold the thermal pad system 800 in place on the user's body.

Figure 10:
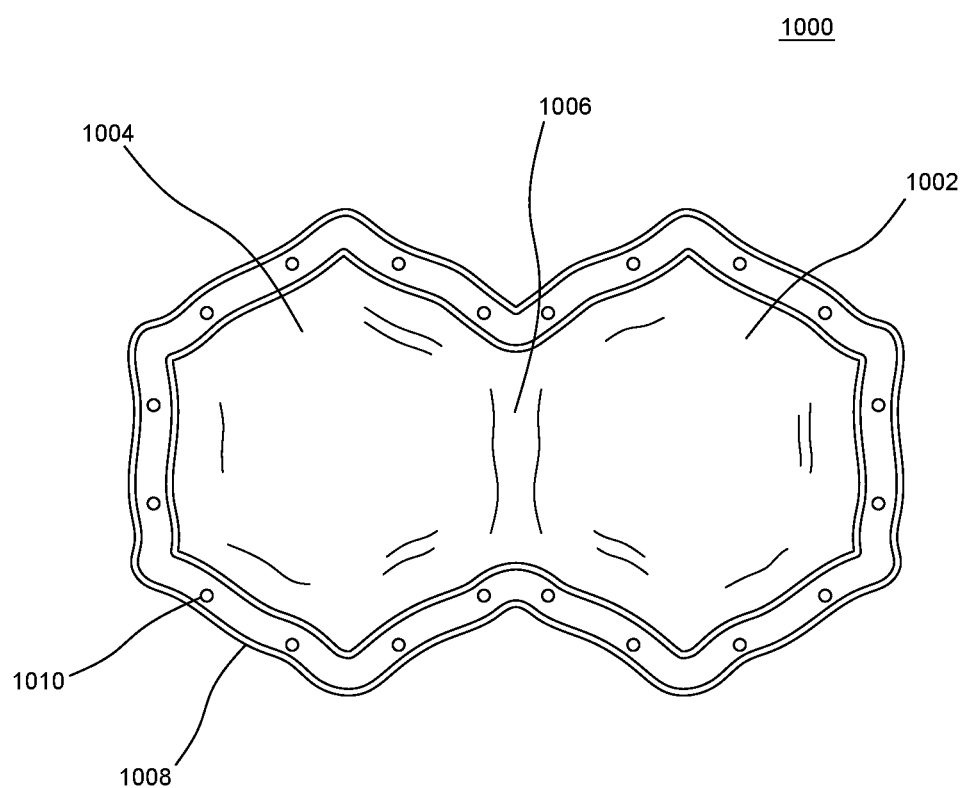
FIG. 10 shows a thermal pad have two distinct contiguous volumes, in accordance with some embodiments.

FIG. 10 shows a thermal pad 1000 have two distinct contiguous volumes 1002, 1004, in accordance with some embodiments. Thermal pad 1000 shows a more complex shape than the previously described thermal pads, but shares the same characteristics. The thermal pad 1000 is generally flat (i.e. relative to the plane of the page of the drawing), but contains two different general volume regions 1002 and 1004. The volume regions 1002, 1004 are the internal volumes between the two sides of the thermal pad, and in this example, they are contiguous, meaning in the middle region 1006 the two volume regions 1002, 1004 transition from one to the other without any barrier. The thermal pad 1000 also includes a fringe portion 1008 that includes at least one linear portion that has at least one opening 1010. In the present example, actually there are ten linear portions around the fringe portion. Each and any of these linear portions can be a joining site with an adjacent thermal pad, as shown, for example, in FIGS. 6A, 6B, 8A, 8B, and 9. A clip can be used to hold adjacent pads together such that their respective volume regions substantially meet and eliminate gaps between the thermal pads.

Figure 11A:
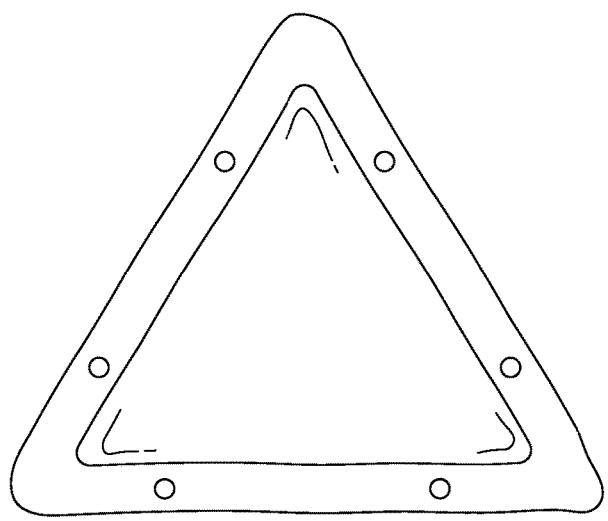
FIGS. 11A-11B show alternative shapes of thermal pads, in accordance with some embodiments.
Figure 11B:
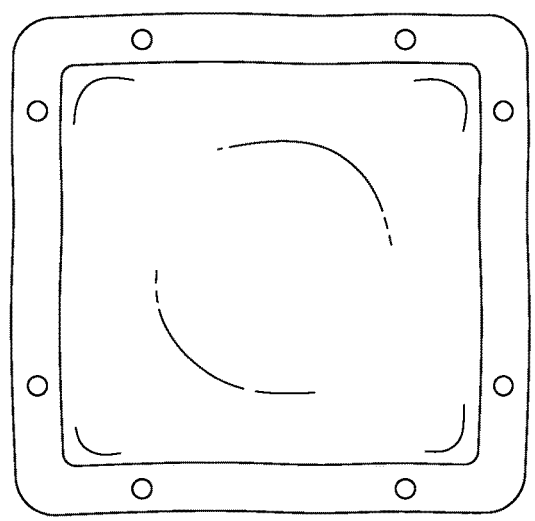

FIGS. 11A-11B show alternative shapes of thermal pads, in accordance with some embodiments. FIG. 11A shows a triangular thermal pad, and FIG. 11B shows a square thermal pad. In general, a thermal pad has a body comprised of two sheet members that each form a side of the thermal pad, and which are joined together around the fringe portion of sheet members. Within the border of the fringe portion the two sheet members are not joined together, but rather, a volume of thermal material is provided between the sheet members within the border. Although the volume of thermal material pushes the two sides of the thermal pad apart, the thermal pad is still substantially flat as the thickness of thermal pad, from one side to the other, is much smaller than the width or length of the thermal pad. Thus, the term "substantially flat" as used here means the thickness, from the exterior surface of one side to the exterior surface of the opposite side through the volume of thermal material is not more than one fifth the length or width across the thermal pad in a direction perpendicular to the thickness dimension. In order to join to thermal pads together such that there is no substantial gap between them, each of the thermal pads must have a section of its fringe portion that matches that of a corresponding fringe portion of the other thermal pad. This is most easily accomplishing using linear sections, such as the sides of a polygon, although it is contemplated that curved sections could also be used, where one thermal pad has a curved section of its fringe portion and another thermal pad has a matching curved fringe portion section (i.e. the complement) so that they can be placed together, and the clip would need to match the curvature of a curved fringe portion sections as well.

It will be appreciated by those skilled in the art that the disclosed thermal pad system allows users to create a variety of shapes by joining pads together at their various sides. Further, the pads can be joined to form three dimensional shapes as well. For example, several thermal pads can be arranged in a line, and then their opposite ends can also be joined together to form a ring of thermal pads that can be used to encircle a body region and apply thermal treatment completely around the body region. Shapes similar to a hat can be arranged that can allow a user to place the thermal pad system over their head. Thus, the system allows an endless variety of shapes to be configured with the thermal pads. The joining method using joining clips that have dimensions that force the adjacent thermal material volumes together so as to substantially eliminate any gap between adjacent pads provides the benefit of more even application of the thermal treatment that eliminates the need to periodically adjust the position of the thermal pad system on the body region being threated.

The claims appended hereto are meant to cover all modifications and changes within the scope and spirit of the present invention.

What is claimed is:

1. A modular thermal pad system, comprising:
    a plurality of thermal pads, each one of the thermal pads having:

a first side and a second side defining a sealed volume between the first side and the second side, the first side and second side being joined together around a perimeter of the sealed volume;
a thermal material disposed in the sealed volume;
a fringe extending from the perimeter of the sealed volume, the fringe having at least one linear section disposed along one of the least one linear edge, the at least one linear section of the fringe having at least one opening therethrough at a first distance from the perimeter;
a joining clip having a first portion and a second portion, each of the first portion and the second portion of the joining clip having a planar surface, the first portion of the joining clip having at least one post extending perpendicularly from the planar surface, the at least one post having a diameter that is about equal to a diameter of the at least one opening through the fringes of the plurality of thermal pads and sized to pass through the at least one opening through the fringes, the second portion of the joining clip having an opening therethrough that is sized to receive the at least one post of the first portion of the joining clip in a snap-fit manner to retain the at least one post;
wherein when a first thermal pad and a second thermal pad of the plurality of thermal pads are positioned adjacent to each other with a fringe of the first thermal pad placed against a fringe of the second thermal pad, and wherein the joining clip holds the fringe of the first thermal pad and the fringe of the second thermal pad together on one side of the first and second thermal pads such that on a second side of the first and second thermal pads opposite the first side a sealed volume of the first thermal pad abuts a sealed volume of the second thermal pad.

2. The modular thermal pad system of claim 1, wherein the first and second thermal pads have a hexagonal shape.

3. The modular thermal pad system of claim 1, wherein the thermal material is a liquid.

4. The thermal pad system of claim 1, further including a first strap clip disposed at an edge of the first thermal pad and a second strap clip disposed at an edge of the second thermal pad.

5. A modular thermal pad system, comprising:
at least two thermal pads including a first thermal pad and a second thermal pad, each of the at least two thermal pads having:
a substantially flat body including a first side member and a second side member, wherein each of the first and second side members are comprised of a respective sheet of material, the first and second side members defining a sealed volume between the first and second side members which is bounded by a border around the sealed volume where the first side member and the second side member are joined together, and wherein the sealed volume of each of the at least two thermal pads is filled with a thermal material;
a fringe extending from the border outward relative to the sealed volume and having a plurality of linear sections around the fringe, wherein each linear section includes at least one opening through the linear section that is spaced a first distance from the border; and
a joining clip having a first portion and a second portion, the first portion having a flat body and at least one post extending perpendicularly from the first portion, the second portion having a flat body and at least one hole through the second portion, and wherein the at least one post is spaced the first distance from an edge of the first portion, and the at least one hole is spaced the first distance from an edge of the second portion;
wherein the joining clip is configured to hold a fringe portion of the first thermal pad together with a corresponding fringe portion of the second thermal pad on a first side of the first and second thermal pad such that the sealed volume of the first thermal pad abuts the sealed volume of the second thermal pad on a second side of the first and second thermal pads.

6. The modular thermal pad system of claim 5, wherein the thermal material in each of the at least two thermal pads is a fluid.

7. The modular thermal pad system of claim 5, wherein the border and fringe of each of the at least two thermal pads are shaped in a regular polygon shape.

8. The module thermal pad system of claim 7, wherein the regular polygon shape is a hexagon.

9. The modular thermal pad system of claim 5, wherein each of the plurality of linear sections of the fringe of each of the at least two thermal pads includes at least two openings.

10. The modular thermal pad system of claim 5, wherein the first and the second portion of the joining clip are coupled together by at least one hinge portion.

11. The thermal pad system of claim 5, further comprising a first strap clip disposed at an edge of a first thermal pad of the at least two thermal pads, and a second strap clip disposed at an opposite edge of a second thermal pad of the at least two thermal pads, wherein each of the first and second strap clips include a post that passes through an opening at the fringe on each of the edge and the opposite edge.

12. A thermal pad system, comprising:
a first thermal pad and a second thermal pad;
each of the first and second thermal pads including:
a first side and a second side, each of the first side and the second side made of a supple material;
a volume formed between the first side and the second containing a thermal material, the volume being defined by a border that is sealed around the volume at a perimeter of the volume;
a fringe, formed by the first side and the second side being bonded together at the border of the volume, that extends outward from the perimeter of the volume to an edge;
a joining clip that gathers a portion of the fringe of the first thermal pad and a portion of the fringe of the second thermal pad together on a same side of the first and second thermal pads and which, as a result, forces the volume of the first thermal pad to abut the volume of the second thermal pad on the opposite side of the first and second thermal pads from the joining clip.

13. The thermal pad system of claim 12, wherein:
the portion of the fringe of the first thermal pad and the portion of the fringe of the second thermal pad gathered by the joining clip each have a hole that is spaced a first distance from the perimeter of the volume of the first and second thermal pads, respectively;
the joining clip has a first portion and a second portion, the first portion having a flat body and at least one post extending perpendicularly from the first portion, the second portion having a flat body and at least one hole through the second portion, and wherein the at least one post is spaced the first distance from an edge of the first portion, and the at least one hole is spaced the first distance from an edge of the second portion.

14. The thermal pad system of claim 13, wherein the first and the second portion of the joining clip are coupled together by at least one hinge portion.

15. The thermal pad system of claim 12, wherein the first and second thermal pads have a hexagonal shape.

16. The thermal pad system of claim 12, wherein the thermal material is a liquid.

17. The thermal pad system of claim 12, further including a first strap clip disposed at an edge of the first thermal pad and a second strap clip disposed at an edge of the second thermal pad.

* * * * *